United States Patent [19]

Kitano

[11] Patent Number: 4,468,390
[45] Date of Patent: Aug. 28, 1984

[54] ANTHELMINTIC COMPOSITION AND THE USE THEREOF

[75] Inventor: Noritoshi Kitano, Tokyo, Japan

[73] Assignee: Sankyo Company, Limited, Tokyo, Japan

[21] Appl. No.: 350,641

[22] Filed: Feb. 22, 1982

[30] Foreign Application Priority Data

Feb. 23, 1981 [JP] Japan ................................. 56-25058

[51] Int. Cl.$^3$ .................. A61K 31/625; A61K 31/335
[52] U.S. Cl. ............................... 424/232; 424/273 B; 424/274; 424/279
[58] Field of Search ............... 424/181, 274, 283, 279, 424/115, 232

[56] References Cited

U.S. PATENT DOCUMENTS 4,144,352 3/1979 Putter .................................. 424/279

OTHER PUBLICATIONS

Campbell et al.–Chem. Abst., vol. 91(1979), p. 32780z.
Takiguchi et al.–Chem. Abst., vol. 95(1981), p. 22942x.
Chabala et al.–Chem. Abst., vol. 93(1980), p. 160,951j.

Primary Examiner—Sam Rosen
Attorney, Agent, or Firm—Frishauf, Holtz, Goodman & Woodward

[57] ABSTRACT

The combined administration of:
(a) one or more macrolide anthelmintic agents selected from the group consisting of B-41 series antibiotics, C-076 series antibiotics and 22,23-dihydro C-076 derivatives; and
(b) one or more anthelmintic agents selected from the group consisting of benzimidazole, salicylamide and isoquinoline compounds, has been bound to exhibit enhanced anthelmintic activity as compared with the additive use of the individual compounds.

14 Claims, No Drawings

ANTHELMINTIC COMPOSITION AND THE USE THEREOF

BACKGROUND TO THE INVENTION

The present invention relates to an anthelmintic composition comprising a mixture of a macrolide antibiotic selected from those of the B-41, C-076 and 22,23-dihydro C-076 series (all of which are known to have anthelmintic activity) with certain other known anthelmintic agents, whereby the anthelmintic activity of the composition is synergistically enhanced.

The compounds referred to herein as "B-41 series antibiotics," "C-076 series antibiotics" and "22,23-dihydro C-076 series antibiotics" are a group of macrolide antibiotics which, despite their different nomenclatures (arising from their different methods of production by various microorganisms), have very closely related molecular structures and activities.

The B-41 series antibiotics were originally isolated from a culture broth of Streptomyces B-41-146 strain (deposited with the Fermentation Research Institute, Agency of Industrial Science and Technology, Ministry of International Trade and Industry, Japan, whence it is available under the Accession No. 1438).

Since the original discovery of the B-41 series compounds, described in British patent specification No. 1,390,336, wherein nine compounds were characterized, a number of other compounds from the same series have been isolated from a culture broth of the same microorganism. As disclosed in this British patent specification, these compounds may be prepared by cultivating a microorganism of the genus Streptomyces, preferably Streptomyces B-41-146 strain, in a suitable culture medium for a period of from 5 to 10 days at about 28° C. under aerobic conditions, after which the culture broth is filtered through diatomaceous earth, the cake obtained is extracted with methanol and then with hexane to given an oily substance and finally the substance is fractionated by column chromatography through silica gel.

The B-41 series compounds thus include compounds having the following formulae (I) or (II), in which the groups represented by $R^1$–$R^6$ are as defined in Tables 1 and 2.

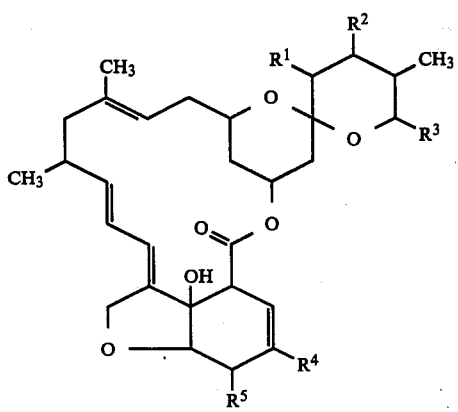

TABLE 1

| B-41 | | $R^1$ | $R^2$ | $R^3$ | $R^4$ | $R^5$ |
|---|---|---|---|---|---|---|
| $\alpha_1$ | (A3) | H | H | CH3 | CH3 | OH |
| $\alpha_2$ | (B2) | H | H | CH3 | CH3 | OCH3 |
| $\alpha_3$ | (A4) | H | H | C2H5 | CH3 | OH |
| $\alpha_4$ | (B3) | H | H | C2H5 | CH3 | OCH3 |
| | (D) | H | H | i-C3H7 | CH3 | OH |
| | (G) | H | H | i-C3H7 | CH3 | OCH3 |
| $\alpha_5$ | (A2) | OH | MH | CH3 | CH3 | OH |
| $\alpha_6$ | (B1) | OH | MH | CH3 | CH3 | OCH3 |
| $\alpha_7$ | | OH | MH | C2H5 | CH3 | OH |
| $\alpha_8$ | | OH | MH | C2H5 | CH3 | OCH3 |
| $\alpha_9$ | (C1) | H | H | CH3 | PC | OH |
| $\alpha_{10}$ | (C2) | H | H | C2H5 | PC | OH |
| | (F) | H | H | i-C3H7 | PC | OH |

In this Table, the following abbreviations are used:
iC3H7—means an isopropyl group;
MH—means a 2-methylhexanoyloxy group of formula

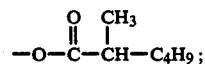

and
PC—means a 2-pyrrolylcarbonyloxymethyl group of formula

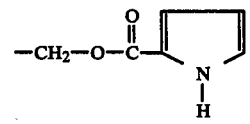

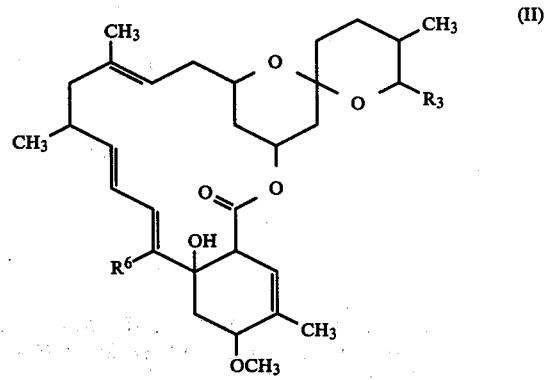

TABLE 2

| B-41 | | $R^3$ | $R^6$ |
|---|---|---|---|
| $\beta_1$ | (A1) | CH3 | CH2OH |
| $\beta_2$ | (A5) | C2H5 | CH2OH |
| | (E) | i-C3H7 | CH2OH |

Of the compounds shown above, those identified as A1, A2, A3, A4, A5, B1, B2, B3, C1 and C2 are described in British patent specification No. 1,390,336. Those compounds identified by α or β are described in The Journal of Antibiotics, 29(3), 76-14 to 76-16 and 29(6), 76-35 to 76-42 and the use of these compounds as anthelmintic agents is described in European Patent Publication No. 2916. Compound B-41D is described in British patent specification No. 2,056,986.

Compounds B-41E and B-41F are described in Japanese Patent Application No. 153,141/80 and Compound B-41G is described in Japanese patent application No. 7091/81.

All of these compounds were obtained from a culture broth of the microorganism Streptomyces strain B-41-146 in the form of an amorphous powder. The properties of Compounds B-41E, B-41F and B-41G are given below.

Compound B-41D

Molecular Weight: 556
Ultraviolet Absorption Spectrum: 237 mμ, 243 mμ.
Infrared Absorption Spectrum: 3450, 1710 cm$^{-1}$.
Nuclear Magnetic Resonance Spectrum δppm:
1.52 (singlet, 14—CH$_3$);
1.86 (broad singlet, 4—CH$_3$);
3.94 (doublet, J=6.2 Hz, 6—H);
4.63 (singlet, 26—CH$_2$);
4.91 (broad triplet, J=8 Hz).
Thin layer chromatography, R$_f$ value: 0.4.

Compound B-41E

Molecular Weight: 572
Ultraviolet Absorption Spectrum: 241 mμ.
Infrared Absorption Spectrum: 3475, 1710 cm$^{-1}$.
Nuclear Magnetic Resonance Spectrum δppm:
1.59 (singlet, 14—CH$_3$);
1.81 (broad singlet, 4—CH$_3$);
3.06 (singlet, 5—OCH$_3$);
4.12 (doubled doublet, J=4.5 and 12 Hz, 26—CH$_2$);
4.30 (doubled doublet, J=6 and 12 Hz, 26—CH$_2$);
4.87 (broad triplet, J=7 Hz, 15—CH=);
6.23 (doubled doublet, J=11 and 12 Hz, 10—CH=);
6.43 (doublet, J=11 Hz, 9—CH=).
Thin layer chromatography, R$_f$ value: 0.61.

Compound B-41F

Molecular Weight: 665
Ultraviolet Absorption Spectrum: 245 mμ, 253 mμ.
Infrared Absorption Spectrum: 3320, 1730, 1710 cm$^{-1}$.
Nuclear Magnetic Resonance Spectrum δppm:
1.48 (singlet, 4—CH$_3$);
3.91 (doublet, J=6 Hz, 6—H);
4.60 (singlet, 26—CH$_2$);
6.1-6.3 (1H, multiplet);
6.8-7.0 (2H, multiplet).
Thin layer chromatography, R$_f$ value: 0.27.

Compound B-41G

Molecular Weight: 570
Ultraviolet Absorption Spectrum: 237 mμ, 244 mμ.
Infrared Absorption Spectrum: 3475, 1715 cm$^{-1}$.
Nuclear Magnetic Resonance Spectrum δppm:
1.50 (singlet, 14—CH$_3$);
1.79 (broad singlet, 4—CH$_3$);
3.44 (singlet, 5—OCH$_3$);
4.59 (singlet, 26—CH$_2$);
4.89 (broad triplet, J=8 Hz, 15—H).
Thin layer chromatography, R$_f$ value: 0.86.

In the above, the infrared absorption spectra were measured in a Nujol-trade mark-mull, the nuclear magnetic resonance spectrum was measured in CDCl$_3$ at a frequency of 100 MHz and the thin layer chromatography was measured on Kieselgel 60 F$_{254}$, using a 18:42 by volume mixture of dioxan and carbon tetrachloride as the developing solvent.

The C-076 series compounds may be obtained from a C-076 producing strain of *Streptomyces avermitilis* (such as that deposited under the Accession No. NRRL8165 at the Agricultural Research Service, Northern Regional Research Laboratory, Peoria, Ill., U.S.A.). The use of these compounds as anthelmintic agents is described in Antimicrobial Agents and Chemotherapy 15, (3), 361-367 (1979). The 22,23-dihydro C-076 compounds and their preparation are described in European patent publication No. 1689.

The C-076 series and 22,23-dihydro C-076 series compounds include those represented by formula (III):

R$^1$-R$^5$ are defined in the following Table 3 and the dotted line between the 22- and 23- positions either represents a single bond or a double bond. Where the dotted line represents a double bond, there are no substituents at the positions indicated by R$^1$ and R$^2$.

TABLE 3

| C-076 | R$^1$ | R$^2$ | R$^3$ | R$^5$ |
|---|---|---|---|---|
| A$_{1a}$ | double bond | | sec-C$_4$H$_9$ | OCH$_3$ |
| A$_{1b}$ | double bond | | i-C$_3$H$_7$ | OCH$_3$ |
| A$_{2a}$ | H | OH | sec-C$_4$H$_9$ | OCH$_3$ |
| A$_{2b}$ | H | OH | i-C$_3$H$_7$ | OCH$_3$ |
| B$_{1a}$ | double bond | | sec-C$_4$H$_9$ | OH |
| B$_{1b}$ | double bond | | i-C$_3$H$_7$ | OH |
| B$_{2a}$ | H | OH | sec-C$_4$H$_9$ | OH |
| B$_{2b}$ | H | OH | i-C$_3$H$_7$ | OH |
| Dihydro A$_{1a}$ | H | H | sec-C$_4$H$_9$ | OCH$_3$ |
| Dihydro A$_{1b}$ | H | H | i-C$_3$H$_7$ | OCH$_3$ |
| Dihydro B$_{1a}$ | H | H | sec-C$_4$H$_9$ | OH |
| Dihydro B$_{1b}$ | H | H | i-C$_3$H$_7$ | OH |

Various benzimidazole compounds (for example Albendazole), salicylamide compounds (e.g., Niclosamide) and isoquinoline compounds (e.g. Praziquantel) are also known to have anthelmintic activity.

However, even the most valuable of therapeutic compounds is rarely free from side effects and, whilst these may not normally be serious, there is, naturally, a desire to reduce them. Clearly, if the anthelmintic activity of the known compounds could be increased without correspondingly increasing the intensity of the side effects, this would be a valuable contribution to the art.

BRIEF SUMMARY OF INVENTION

We have now surprisingly discovered that the joint use of one or more of the B-41 series antibiotics, the C-076 series antibiotics or the 22,23-dihydro C-076 series antibiotics with one or more other anthelmintic agents selected from benzimidazole, salicylamide and isoquinoline compounds substantially enhances anthelmintic activity synergistically, without a corresponding increase in the intensity of side effects. As a result, it is possible to reduce substantially the dose of the anthelmintic agent and thus reduce side effects, such as intoxication.

Accordingly, in one aspect, the invention provides a composition comprising:
(a) one or more anthelmintic agents selected from the group consisting of the B-41 series antibiotics, the C-076 series antibiotics and the 22,23-dihydro C-076 series antibiotics; and
(b) one or more other anthelmintic agents selected from the group consisting of benzimidazole, salicylamide and isoquinoline compounds.

The invention also provides a method of treating a human or other animal infested with helminths, which comprises administering to that human or other animal:
(a) one or more anthelmintic agents selected from the group consisting of B-41 series antibiotics, C-076 series antibiotics and 22,23-dihydro C-076 series antibiotics; and
(b) one or more other anthelmintic agents selected from the group consisting of benzimidazole, salicylamide and isoquinoline compounds.

DETAILED DESCRIPTION OF INVENTION

Examples of suitable benzimidazole series anthelmintic agents which may be used in the composition and method of the present invention include, for example:
2-(Methoxycarbonylamino)benzimidazole;
5-Butyl-2-(methoxycarbonylamino)benzimidazole;
5-Propoxy-2-(methoxycarbonylamino)benzimidazole;
5-Ethoxy-2-(ethoxycarbonylamino)benzimidazole;
5-Propylthio-2-(methoxycarbonylamino)benzimidazole;
5-Phenylthio-2-(methoxycarbonylamino)benzimidazole;
5-Phenylsulphinyl-2-(methoxycarbonylamino)benzimidazole;
5-(2,4-Dichlorophenoxy)-6-chloro-2-methylthiobenzimidazole;
6-Chloro-5-(2,3-dichlorophenoxy)-2-methylthiobenzimidazole;
2-(4-Thiazolyl)benzimidazole; and
5-Isopropoxycarbonylamino-2-(4-thiazolyl)benzimidazole.

Suitable salicylamide series anthelmintic agents which may be used in the composition and method of the present invention include, for example:
5-Chloro-N-(2-chloro-4-nitrophenyl)salicylamide;
3,5-Diiodo-N-(3-chloro-4-p-chlorophenoxyphenyl)salicylamide;
3,5-Diiodo-N-[5-chloro-2-methyl-4-(α-cyano-4-chlorobenzyl)phenyl]salicylamide;
3,5,6-Trichloro-N-(3,5-dichloro-2-hydroxyphenyl)salicylamide;
2-Acetoxy-3,5-diiodo-N-(p-chlorophenyl)benzamide; and
2-Acetoxy-3-bromo-5-chloro-N-(p-bromophenyl)thiobenzamide.

Suitable isoquinoline series anthelmintic agents, which may be used in the composition and method of the present invention include, for example, 1-isomers of:
2-Cyclohexylcarbonyl-4-oxo-1,2,3,6,7,11b-hexahydro-4H-pyrazino[2,1-a]isoquinoline; and
2-Benzoyl-4-oxo-1,2,3,6,7,11b-hexahydro-4H-pyrazino[2,1-a]isoquinoline.

These isoquinoline compounds may be represented by the formula (IV):

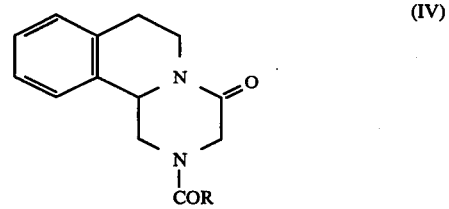

in which R represents a cyclohexyl or phenyl group, respectively.

Particularly preferred are combinations of B-41D, C-076 $B_{1a}$, C-076 $B_{1b}$, 22,23-dihydro C-076 $B_{1a}$ or 22,23-dihydro C-076 $B_{1b}$, with one or more of the abovementioned benzimidazole, salicylamide or isoquinoline series compounds.

The anthelmintic compositions of the invention are useful as parasiticides for the treatment of human beings and other animals. They are particularly useful for the treatment of diseases in livestock, poultry and pet animals (such as pigs, sheep, goats, cows, horses, dogs, cats and chickens) caused by the group of parasites known as the Nematoda, especially those of genera:
Haemonchus;
Trichostrongylus;
Ostertagia;
Nematodirus;
Cooperia;
Ascaris;
Bunostomum;
Oesophagostomum;
Chabertia;
Trichuris;
Strongylus;
Trichonema;
Dictyocaulus;
Capillaria;
Heterakis;
Toxocara;
Ascaridia;
Oxyuris;
Ancylostoma;
Uncinaria;
Toxascaris; and
Parascaris.

Some of the parasites of the genera Nematodirus, Cooperia and Oesophagostomum attack the intestines, whereas parasites of the genera Haemonchus and Ostertagia attack the stomach and parasites of the genus Dictyocaulus are found in the lungs. Parasites of the families Filariidae or Setariidae are found in the heart, the blood vessels and tissues and organs such as the subcutaneous tissues and lymphatic vessels.

The compositions of the invention may also be used for the treatment of diseases caused by, for example, the following Cestoidea:

Taenia saginata;
Hymenolepis diminuta;
Hymenolepis nana;
Moniezia benedeni;
Diphyllobothrium latum;
Diphyllobothrium erinacei;
Echinococcus glanulosus; and
Echinococcus multilocularis, and caused by the following Trematoda;

Fasciola hepatica;
Fasciola gigantica;
Paragonimus westermanii;
Fasciolopsis buski;
Eurytrema pancreaticum;
Eurytrema coelomaticum;
Clonorchis sinensis;
Schistosoma japonicum;
Schistosoma haematobium; and
Schistosoma mansoni.

The anthelmintic compositions of the invention may be administered orally. One suitable oral formulation is as a drink, in which case the composition may be formulated as an aqueous solution, as a solution in another suitable non-toxic solvent or as a suspension or dispersion incorporating a suspension aid and a wetting agent (such as bentonite) or other constituents.

The composition of the invention may also be administered as a solid, suitably in unit dosage form, for example as a capsule, pill or tablet containing a predetermined amount of the active ingredients. These formulations can be prepared by homogeneously mixing the active ingredients with one or more other finely pulverized materials, generally diluents, filling agents, disintegrators and/or binding agents (e.g. starch, lactose, talc, magnesium stearate or vegetable gum). The weight and content of the active ingredients in such unit dosage forms may vary widely, depending upon the type of animal to be treated, the degree of infection, the kind of parasite and the body weight of the animal.

The anthelmintic compositions of the invention may also be administered to animals by uniformly dispersing them in their feed or they may be used a top dressing or in the form of pellets.

The active ingredients may also be dissolved or dispersed in a liquid carrier and administered parenterally to animals by injection into the proventriculus, the muscles, the lungs or under the skin. For parenteral administration, the carrier used is preferably a vegetable oil, such as peanut oil or cottonseed oil.

Topical administration of the compositions of the invention is also possible, in which case the active ingredients are preferably mixed with a suitable carrier (such as dimethyl sulphoxide or a hydrocarbon solvent). The resulting formulation can be directly applied to the outer skin of the animals, e.g. by spraying.

The optimum amount of the active ingredients of the composition of the invention desired to achieve best results will vary depending upon the kind of animal to be treated, the type of parasitic infection and the degree of infection. However, in general, we have found that good results are achieved by using from 0.01 to 100 mg, preferably from 0.1 to 50 mg, of the B-41, C-076 or 22,23-dihydro C-076 series antibiotics and from 0.5 to 200 mg, preferably from 1to 30 mg, of the benzimidazole, salicylamide or isoquinoline compound, per kg body weight for oral administration.

The enhanced activities of the compositions of the invention are illustrated by the following Examples.

EXAMPLE 1

The test animals used in this Example were goats (two per test group) parasitized by Haemonchus contortus, Ostertagia ostertagi and Fasciola species.

Each goat was given a single gelatin capsule containing the amount of B-41D and/or Albendazole [i.e. 5-propylthio-2-(methoxycarbonylamino)benzimidazole] shown in Table 4. The number of eggs per gram of faeces (E.P.G.) before and after administration was determined. 14 days after administration, the goats were sacrificed and the number of living parasites was determined. These results are also shown in Table 4.

The names of the parasites are abbreviated in the Table as follows:

H.c = Haemonchus contortus
O.o = Ostertagia ostertagi
F.sp. = Fasciola species

TABLE 4

Anthelmintic efficacy in goats by single and joint use of B-41D with Albendazole against Haemonchus contortus, Ostertagia osteragi and Fasciola sp.

| Compound and amount (mg/kg) | | E.P.G. of H.c and O.o | | | E.P.G. of F.sp. | | Number of living parasites at autopsy | | | Reduction rate (%) | | |
|---|---|---|---|---|---|---|---|---|---|---|---|---|
| | | before administr. | after administr. 7 days | after administr. 14 days | before administr. | after administr. 14 days | H.c | O.o | F.sp. | H.c | O.o | F.sp. |
| B-41D | 0.2 | 3200 | 0 | 0 | 450 | 990 | 0 | 0 | 21 | 100 | 100 | 32.0 |
| | | 4400 | 0 | 0 | 880 | 620 | 0 | 0 | 13 | | | |
| B-41D | 0.05 | 3400 | 0 | 100 | 1320 | 940 | 78 | 455 | 19 | 68.2 | 70.5 | 34.0 |
| | | 2000 | 0 | 80 | 480 | 860 | 51 | 431 | 14 | | | |
| B-41D + | 0.05 +4300 | 0 | 0 | 920 | 0 | 0 | 0 | 0 | 100 | 100 | 100 | |
| Albendazole | 2.5 | 600 | 0 | 0 | 810 | 0 | 0 | 0 | 0 | | | |
| B-41D + | 0.05 + | 3800 | 0 | 0 | 1100 | 0 | 0 | 0 | 100 | 100 | 100 | |
| Albendazole | 5 | 2900 | 0 | 0 | 540 | 0 | 0 | 0 | 0 | | | |
| Albendazole | 5 | 3300 | 0 | 0 | 760 | 20 | 0 | 0 | 8 | 100 | 100 | 72.0 |
| | | 900 | 0 | 0 | 320 | 10 | 0 | 0 | 6 | | | |
| None | | 2100 | 4210 | 3600 | 1800 | 1980 | 162 | 1022 | 27 | | | |
| | | 3700 | 3100 | 2800 | 1710 | 1220 | 244 | 1982 | 23 | | | |

EXAMPLE 2

The animals used in this Example were dogs (two per test group) parasitized by *Toxocara canis* (T.c), *Ancylostoma caninum* (A.c) and *Dipylidium caninum* (D.c). Each dog was given a single gelatin capsule containing the prescribed amounts of B-41D and/or Niclosamide [i.e. 5-chloro-N-(2-chloro-4-nitrophenyl)salicylamide], as shown in Table 5. The E.P.G. and the number of parasites excreted before and after administration were determined. The dogs were sacrificed 7 days after administration and the number of living parasites was determined. It was confirmed that *Dipylidium caninum* excreted its segments in the faeces before administration of the drugs.

The results are shown in Table 5.

TABLE 5

Anthelmintic efficacy in dogs by singe and joint use of B-41D with Niclosamide against *Toxocara canis*, *Ancylostoma caninum* and *Dipylidium caninum*

| Compound and amount (mg/kg) | | E.P.G. before administr. | | E.P.G. after administr. (7 days) | | Number of excreted parasites (for 7 days) | | Number of living parasites at autopsy | | | Reduction rate (%) | | |
|---|---|---|---|---|---|---|---|---|---|---|---|---|---|
| | | T.c | A.c | T.c | A.c | T.c | A.c | T.c | A.c | D.c | T.c | A.c | D.c |
| B-41D | 0.1 | 13400 | 1400 | 0 | 0 | 24 | 13 | 0 | 0 | 16 | 100 | 100 | 23.2 |
| | | 600 | 900 | 0 | 0 | 9 | 8 | 0 | 0 | 27 | | | |
| B-41D | 0.025 | 2100 | 750 | 0 | 30 | 7 | 9 | 3 | 3 | 11 | 67.8 | 71.4 | 23.2 |
| | | 8400 | 1100 | 0 | 100 | 12 | 11 | 6 | 5 | 32 | | | |
| B-41D + | 0.025+ | 2600 | 500 | 0 | 0 | 13 | 10 | 0 | 0 | 0 | 100 | 100 | 100 |
| Niclosamide | 75 | 600 | 450 | 0 | 0 | 4 | 16 | 0 | 0 | 0 | | | |
| B-41D + | 0.025+ | 1800 | 350 | 0 | 0 | 8 | 6 | 0 | 0 | 0 | 100 | 100 | 100 |
| Niclosamide | 150 | 1500 | 1450 | 0 | 0 | 9 | 23 | 0 | 0 | 0 | | | |
| Niclosamide | 150 | 3200 | 2100 | 2600 | 1200 | 0 | 1 | 6 | 14 | 8 | 13.0 | 31.0 | 73.2 |
| | | 4100 | 800 | 3100 | 450 | 0 | 0 | 14 | 6 | 7 | | | |
| None | | 2400 | 2300 | 1800 | 3400 | 0 | 0 | 8 | 21 | 37 | | | |
| | | 2100 | 850 | 3400 | 1600 | 0 | 0 | 15 | 8 | 19 | | | |

EXAMPLE 3

The test animals used in this Example were dogs (two per test group) parasitized by *Trichuris vulpis* (T.v) and *Dipylidium caninum* (D.c). Each dog was given a single gelatin capsule containing the prescribed amount of B-41D and/or Praziquantel (i.e. 1-2-cyclohexylcarbonyl-4-oxo-1,2,3,6,7,11b-hexahydro-4H-pyrazino[2.1-a]isoquinoline). The E.P.G. and number of parasites before and after administration were determined. The dogs were sacrificed 7 days after administration and the number of living parasites was also determined. It was confirmed that *Dipylidium caninum* excreted its segments in the faeces before administration of the drugs. The results are shown in Table 6.

TABLE 6

Anthelmintic efficacy in dogs by single and joint use of B-41D with Praziquantel against *Trichuris vulpis* and *Dipylidium caninum*

| Compound and amount (mg/kg) | | E.P.G. of T.v. before administr. | E.P.G. of T.v. after administr. (7 days) | Number of excreted parasites (for 7 days) | Number of living parasites at autopsy | | Reduction rate (%) | |
|---|---|---|---|---|---|---|---|---|
| | | | | | T.v. | D.c. | T.v. | D.c. |
| B-41D | 0.1 | 800 | 0 | 68 | 0 | 17 | 100 | 16.6 |
| | | 100 | 0 | 18 | 0 | 28 | | |
| B-41D | 0.05 | 1600 | 300 | 181 | 58 | 9 | 75.1 | 22.2 |
| | | 900 | 200 | 88 | 31 | 33 | | |
| B-41D + | 0.05 + | 300 | 0 | 0 | 0 | 0 | 100 | 100 |
| Praziquantel | 2.5 | 1400 | 0 | 0 | 0 | 0 | | |
| B-41D + | 0.05 + | 500 | 0 | 0 | 0 | 0 | 100 | 100 |
| Praziquantel | 5 | 200 | 0 | 0 | 0 | 0 | | |
| Praziquantel | 5 | 700 | 300 | 0 | 142 | 6 | — | 77.7 |
| | | 600 | 800 | 0 | 263 | 6 | | |
| None | | 1100 | 600 | 0 | 165 | 32 | | |
| | | 700 | 400 | 0 | 97 | 22 | | |

From the above results, it is apparent that B-41D, when used alone is ineffective against Trematoda (such as the liver fluke) but, when used together with Albendazole, the combination shows more activity than does Albendazole alone.

Niclosamide alone is ineffective against such Nematoda as *Toxocara canis* and *Ancylostoma caninum* whilst B-41D alone is ineffective against *Dipylidium caninum*, but the combination of the two compounds shows more activity against all of these parasites than do the respective active compounds when used alone.

Praziquantel alone is ineffective against such Nematodae as *Trichuris vulpis* but, when it is used jointly with B-41D, the combination shows greater activity than B-41D against both Nematoda and Cestoida Moreover, the compounds, when used jointly, are effective in much smaller doses than are the compounds when used alone, thus strongly suggesting the presence of synergism.

I claim:

1. An anthelmintic composition comprising:
    (a) an effective amount of one or more macrolide anthelmintic agents selected from the group consisting of B-41 series antibiotics, C-076 series antibiotics and 22,23-dihydro C-076 series compounds; and (b) an effective amount of one or more anthelmintic agents selected from the group consisting of benzimidazole, salicylamide and isoquinoline compounds.

2. The composition as claimed in claim 1, wherein said macrolide anthelmintic agent (a) is B-41D.

3. The composition as claimed in claim 1, wherein the macrolide anthelmintic agent (a) is C-076 $B_{1a}$, C-076 $B_{1b}$, 22,23-dihydro C-076 $B_{1a}$ or 22,23-dihydro C-076 $B_{1b}$.

4. The composition as claimed in claim 1, wherein the benzimidazole, salicylamide and isoquinoline compounds are selected from the group consisting of;
2-(Methoxycarbonylamino)benzimidazole;
5-Butyl-2-(methoxycarbonylamino)benzimidazole;
5-Propoxy-2-(methoxycarbonylamino)benzimidazole;
5-Ethoxy-2-(ethoxycarbonylamino)benzimidazole;
5-Propylthio-2-(methoxycarbonylamino)benzimidazole;
5-Phenylthio-2-(methoxycarbonylamino)benzimidazole;
5-Phenylsulphinyl-2-(methoxycarbonylamino)benzimidazole;
5-(2,4-Dichlorophenoxy)-6-chloro-2-methylthiobenzimidazole;
6-Chloro-5-(2,3-dichlorophenoxy)-2-methylthiobenzimidazole;
2-(4-Thiazolyl)benzimidazole;
5-Isopropoxycarbonylamino-2-(4-thiazolyl)benzimidazole;
5-Chloro-N-(2-chloro-4-nitrophenyl)salicylamide;
3,5-Diiodo-N-(3-chloro-4-p-chlorophenoxyphenyl)salicylamide;
3,5-Diiodo-N-[5-chloro-2-methyl-4-(α-cyano-4-chlorobenzyl)phenyl]salicylamide;
3,5,6-Trichloro-N-(3,5-dichloro-2-hydroxyphenyl)salicylamide;
2-Acetoxy-3,5-diiodo-N-(p-chlorophenyl)benzamide;
2-Acetoxy-3-bromo-5-chloro-N-(p-bromophenyl)thiobenzamide;
2-Cyclohexylcarbonyl-4-oxo-1,2,3,6,7,11b-hexahydro-4H-pyrazino[2,1-a]isoquinoline; and
2-Benzoyl-4-oxo-1,2,3,6,7,11b-hexahydro-4H-pyrazino[2,1-a]isoquinoline.

5. The composition as claimed in claim 1, wherein B-41 series antibiotics is B-41D and the benzimidazole, salicylamide and isoquinoline compounds are selected from the group consisting of;
2-(Methoxycarbonylamino)benzimidazole;
5-Butyl-2-(methoxycarbonylamino)benzimidazole;
5-Propoxy-2-(methoxycarbonylamino)benzimidazole;
5-Ethoxy-2-(ethoxycarbonylamino)benzimidazole;
5-Propylthio-2-(methoxycarbonylamino)benzimidazole;
5-Phenylthio-2-(methoxycarbonylamino)benzimidazole;
5-Phenylsulphinyl-2-(methoxycarbonylamino)benzimidazole;
5-(2,4-Dichlorophenoxy)-6-chloro-2-methylthiobenzimidazole;
6-Chloro-5-(2,3-dichlorophenoxy)-2-methylthiobenzimidazole;
2-(4-Thiazolyl)benzimidazole;
5-Isopropoxycarbonylamino-2-(4-thiazolyl)benzimidazole;
5-Chloro-N-(2-chloro-4-nitrophenyl)salicylamide;
3,5-Diiodo-N-(3-chloro-4-p-chlorophenoxyphenyl)salicylamide;
3,5-Diiodo-N-[5-chloro-2-methyl-4-(α-cyano-4-chlorobenzyl)phenyl]salicylamide;
3,5,6-Trichloro-N-(3,5-dichloro-2-hydroxyphenyl)salicylamide;
2-Acetoxy-3,5-diiodo-N-(p-chlorophenyl)benzamide;
2-Acetoxy-3-bromo-5-chloro-N-(p-bromophenyl)thiobenzamide;
2-Cyclohexylcarbonyl-4-oxo-1,2,3,6,7,11b-hexahydro-4H-pyrazino[2,1-a]isoquinoline; and
2-Benzoyl-4-oxo-1,2,3,6,7,11b-hexahydro-4H-pyrazino[2,1-a]isoquinoline.

6. The composition as claimed in claim 1, comprising B-41D and 5-propylthio-2-(methoxycarbonylamino)benzimidazole.

7. The composition as claimed in claim 1, comprising B-41D and 5-chloro-N-(2-chloro-4-nitrophenyl)salicylamide.

8. The composition as claimed in claim 1, comprising B-41D and 1-2-cyclohexylcarbonyl-4-oxo-1,2,3,6,7,11b-hexahydro-4H-pyrazino[2,1-a]isoquinoline.

9. A method of treating a human or other animal infested with helminths, which comprises administering:
(a) an effective amount of one or more macrolide anthelmintic agents selected from the group consisting of B-41 series antibiotics, C-076 series antibiotics and 22,23-dihydro C-076 series compounds; and
(b) an effective amount of one or more anthelmintic agents selected from the group consisting of benzimidazole, salicylamide and isoquinoline compounds.

10. The method as claimed in claim 7, wherein said macrolide anthelmintic agent (a) is B-41D.

11. The method as claimed in claim 7, wherein the macrolide anthelmintic agent (a) is C-076 $B_{1a}$, C-076 $B_{1b}$, 22,23-dihydro C-076 $B_{1a}$ or 22,23-dihydro C-076 $B_{1b}$.

12. The method as claimed in claim 7, wherein there is administered B-41D and 5-propylthio-2-(methoxycarbonylamino)benzimidazole.

13. The method as claimed in claim 7, wherein there is administered B-41D and 5-chloro-N-(2-chloro-4-nitrophenyl)salicylamide.

14. The method as claimed in claim 7, wherein there is administered B-41D and 1-2-cyclohexylcarbonyl-4-oxo-1,2,3,6,7,11b-hexahydro-4H-pyrazino[2,1-a]isoquinoline.

* * * * *

UNITED STATES PATENT AND TRADEMARK OFFICE
CERTIFICATE OF CORRECTION

PATENT NO. : 4,468,390
DATED : August 28, 1984
INVENTOR(S) : Noritoshi KITANO

It is certified that error appears in the above-identified patent and that said Letters Patent is hereby corrected as shown below:

```
Columns 7 and 8 - Table 4:
    second column, eighth line from bottom, after
    "+", delete "4300".

third column, ninth line from bottom, under
    "2000" replace "0" with --4300--.

fifth column, ninth line from bottom, under
    "80" replace "920" with --0--.

sixth column, ninth line from bottom, under
    "480" replace "0" with --920--.

tenth column, sixth line from bottom, under
    "0" replace "100" with --0--.

last column, sixth line from bottom, insert --100--.
```

Signed and Sealed this

Fourteenth Day of January 1986

[SEAL]

Attest:

DONALD J. QUIGG

Attesting Officer

Commissioner of Patents and Trademarks